United States Patent [19]
Terauchi et al.

[11] Patent Number: 4,746,757
[45] Date of Patent: May 24, 1988

[54] PROCESS FOR PRODUCING (2-HYDROXY-2-PROPYL)-NAPHTHALENE COMPOUNDS

[75] Inventors: Takashi Terauchi; Tadashi Nakamura; Shoichi Hoshi, all of Iwaki, Japan

[73] Assignee: Kureha Kagaku Kogyo Kabushiki Kaisha, Tokyo, Japan

[21] Appl. No.: 887,119

[22] Filed: Jul. 17, 1986

[30] Foreign Application Priority Data

Jul. 19, 1985 [JP] Japan .................. 60-159924

[51] Int. Cl.$^4$ ............................. C07C 27/16
[52] U.S. Cl. ....................... 568/815
[58] Field of Search ..................... 568/815

[56] References Cited

U.S. PATENT DOCUMENTS

| | | | |
|---|---|---|---|
| 2,438,125 | 3/1948 | Lorand et al. | 568/811 |
| 2,548,435 | 4/1951 | Lorand et al. | 568/815 |
| 2,634,294 | 4/1953 | Butler | 568/815 |
| 2,713,599 | 7/1955 | Lorand et al. | 568/815 |
| 3,382,286 | 5/1968 | Griffin | 568/812 |
| 3,385,897 | 5/1968 | Vanderwerff | 568/815 |
| 3,567,786 | 3/1971 | Bastian | 568/815 |
| 3,666,815 | 5/1972 | Scheltus | 568/815 |
| 3,914,295 | 10/1975 | Rosenthal et al. | 568/815 |

FOREIGN PATENT DOCUMENTS

| | | | |
|---|---|---|---|
| 1093156 | 5/1986 | Japan | 568/815 |
| 0980272 | 1/1965 | United Kingdom | 568/815 |
| 2159154 | 11/1985 | United Kingdom | 568/815 |

OTHER PUBLICATIONS

C. Arnoldi, A. Citterio and F. Minisci, J. Chem. Soc. Perkin Trans. II, 1983, 531–541.
A. Ledwith and P. J. Russell, J.C.S. Chem. Comm., 1984, 291–292.
K. Ogawa and Y. Nomura, Org. Synth. Chem., vol. 42, 1984, 98–114.
Giordano et al., "Tetrahedron" vol. 36 (1980), pp. 3559–3562.
Jonsson et al., "J.C.S. Perkins I" (1979), pp. 669–672.
Walling et al., "J. Amer. Chem. Soc." vol. 97(6), (1975).

*Primary Examiner*—Werren B. Lone
*Attorney, Agent, or Firm*—John P. White

[57] ABSTRACT

Disclosed herein is a process for producing (2-hydroxy-2-propyl)naphthalene compounds, comprising oxidizing a naphthalene compound having isopropyl group(s) on the naphthalene ring in the presence of peroxodisulfate in a mixed solvent of water and an organic polar solvent.

8 Claims, No Drawings

PROCESS FOR PRODUCING (2-HYDROXY-2-PROPYL)-NAPHTHALENE COMPOUNDS

BACKGROUND OF THE INVENTION

The present invention relates to a novel process for producing a naphthalene compound having 2-hydroxy-2-propyl group(s) on the naphthalene ring, that is, (2-hydroxy-2-propyl)naphthalene compound (hereinafter referred to as HPN).

HPN produced according to the present invention is easily convertible into a compound useful as a raw material for plastics, particularly as a raw material for engineering plastics, for instance, 2,6-naphthalenediol.

Recently, various polymers have been developed as engineering plastics, and among them, aromatic polyesters obtained by using naphthalene derivatives having hydroxy group(s) or carboxyl group(s) as raw material have attracted one's attention because of their excellent heat-resistance and mechanical strength. Accordingly, the development of an industrially profitable process for producing the naphthalene derivative having hydroxy group(s) or carboxyl group(s) which is used as the raw material of the aromatic polyesters has been demanded.

Since the naphthalene derivative having hydroxy group(s) or carboxyl group(s) can be easily produced from the HPN, for instance, 2,6-naphthalenediol is easily available in a high yield by oxidizing 2,6-di(2-hydroxy-2-propyl)naphthalene with hydrogen peroxide in acetonitrile or 1,4-dioxane in the presence of an inorganic acid (refer to Japanese Patent Application No. 60-123819 (1985)), the usefulness of HPN as an intermediate raw material has been raised.

As a process for converting an isopropyl group bonded to a naphthalene ring into a 2-hydroxy-2-propyl group by oxidation, a process which comprises oxidizing with molecular oxygen in the presence of an aqueous alkali solution, for example, Japanese Patent Publication No. 39-21242 (1964), has been proposed, and as a process for converting an isopropyl group bonded to a benzene ring into the 2-hydroxy-2-propyl group, a process has been proposed in Japanese Patent Publication No. 39-19355 (1964), Japanese Patent Application Laying-Open (KOKAI) No. 58-162539 (1983) and DE-OS No. 12 33 839. However, no process in which peroxodisulfate is used as an oxidizing agent has been known.

As has been described above, under the circumstances, any industrially profitable process for producing HPN has not been established and there are very few research reports on such a process despite of the increased industrial usefulness of HPN.

As a result of the present inventors' studies, it has been found by the present inventors that (1) a naphthalene compound having isopropyl group(s) on the naphthalene ring (isopropylnaphthalene compound) is easily oxidized into HPN in the presence of peroxodisulfate in a mixed solvent of water and an organic polar solvent, (2) the yield of HPN can be raised in the case where the oxidation is carried out in the presence of iron (II) salt and/or chloride and (3) in the case where a naphthalene compound having two or more isopropyl groups on the naphthalene ring is used as a starting material, an oxidation product of a different stage of oxidation can be selectively obtained by selecting a proper reaction condition, and on the basis of the findings, the present inventors have accomplished the present invention.

DETAILED DESCRIPTION OF THE INVENTION

The present invention relates to a process for oxidizing an isopropyl group bonded to a naphthalene ring into a 2-hydroxy-2-propyl group in the presence of peroxodisulfate in a mixed solvent of an organic polar solvent and water, and more in detail, the present invention relates to (1) a process for producing (2-hydroxy-2-propyl)naphthalene compound (HPN) by oxidizing a isopropylnaphthalene compound (hereinafter referred to as IPN) in the presence of peroxodisulfate in a mixed solvent of an organic polar solvent and water, and (2) a process wherein the oxidation by peroxodisulfate ions is carried out in the presence of iron (II) salt and/or chloride.

The isopropylnaphthalene compound (IPN) used in the present invention as the starting material is a derivative of naphthalene having at least one isopropyl group on the naphthalene ring, and IPN may have a plurality of isopropyl groups and/or one or a plurality of substituents other than isopropyl group, for instance, —COOH,

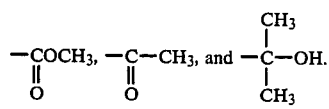

As such an IPN according to the present invention, monoisopropylnaphthalene, diisopropylnaphthalene and isopropylnaphthalenecarboxylic acid may be exemplified.

The organic polar solvent used in the present invention may be an organic polar solvent which dissolves IPN as the starting material and is miscible with water and may be selected from a wide variety of solvents such as nitriles, ketones, aldehydes, carboxylic acids, alcohols, esters, amides, ethers, sulfoxides and fluorocarbons, however, acetonitrile, acetone and acetic acid are particularly preferable.

According to the present invention, IPN as the starting material is dissolved in a mixed solvent of the organic polar solvent and water, and after adding peroxodisulfate into the thus formed solution, IPN in the mixture is subjected to oxidation while vigorously stirring the mixture.

As the peroxodisulfate, ammonium peroxodisulfate, sodium peroxodisulfate, potassium peroxodisulfate, etc., may be used, and an aqueous solution of the peroxodisulfate is added to the solution of IPN or the peroxodisulfate is dissolved in advance into the mixed solvent.

The ratio of the amount of water to the amount of the organic polar solvent in the mixed solvent is not particularly limited so far as dissolving IPN and the peroxodisulfate, however, in general, the ratio is preferably from 1:1 to 1:10.

The concentration of IPN in the reaction system is not particularly limited, however, ordinarily, the oxidation is carried out at a concentration of IPN in a range of from 0.01 to 50% by weight, preferably from 0.1 to 20% by weight.

The peroxodisulfate may be used in an amount of from 0.05 to 10 mols, preferably from 0.1 to 5 mols per one mol of the isopropyl group in the reaction system.

As has been described above, HPN is available by subjecting IPN to oxidation in the presence of peroxodisulfate in a mixed solvent of an organic polar solvent and water, and in the present invention, it is possible to improve the conversion of the starting material, IPN, and the yield of HPN by carrying out the oxidation in the presence of iron (II) salt and/or chloride.

As the iron (II) salt, iron (II) sulfate heptahydrate and iron (II) chloride may be exemplified, and as the chloride, sodium chloride may be exemplified.

The amount of addition of the iron (II) salt is not less than 0.001 mol per one mol of the isopropyl group of IPN, preferably from 0.01 to 6 mols, and the amount of addition of the chloride is not less than 0.01 mol as chloride ion, preferably from 0.1 to 25 mols per one mol of the isopropyl group of IPN.

Also in the case where the iron (II) salt and/or the chloride are used, as far as the mixed solvent can dissolve IPN, the peroxodisulfate, the iron (II) salt and/or the chloride, the ratio of the amount of water to the amount of the organic polar solvent in the mixed solvent is not particularly limited, however, it is preferable that the above-mentioned ratio is from 1:0.1 to 1:10.

In addition, since a part of Fe(II) ions in the reaction system is oxidized into Fe(III) ions by peroxodisulfate ions, the previous presence of Fe(III) ions in the reaction system does not affect the reaction.

As for the reaction conditions in the process according to the present invention, in general, the reaction temperature may be selected from the range of from 0° to 120° C., the reaction time may be selected from the range of from one minute to 50 hours and the mixed solvent may be preferably used in an amount which is sufficient for dissolving the whole amounts of IPN, the peroxodisulfate as well as the iron (II) salt and/or the chloride.

In the case where a naphthalene compound having two or more isopropyl groups is used as the starting material, several kinds of oxidation products of different oxidation stages are produced, however, by suitably selecting the reaction conditions, it is possible to selectively obtain the desired oxidation product. For instance, in the case where 2,6-diisopropylnaphthalene is used as the starting material, 2-(2-hydroxy-2-propyl)-6-isopropylnaphthalene; 2,6-di(2-hydroxy-2-propyl)naphthalene and 2-(2-hydroxy-2-propyl)-6-acetylnaphthalene may be produced, however, in the case where 2-(2-hydroxy-2-propyl)-6-isopropylnaphthalene is mainly desired, the mild reaction conditions may be preferable. On the other hand, in the case where 2-(2-hydroxy-2-propyl)-6-acetylnaphthalene is mainly desired, severer reaction conditions are necessary.

In addition, in carrying out the process of the present invention, the reaction may be carried out in an oxygen atmosphere (including an aerial atmosphere) or in an inert atmosphere, and the reaction pressure is not particularly limited. Further, the reaction may be operated batchwisely or continuously, and after finishing the reaction, the thus formed HPN is available according to ordinary steps of separation and purification including neutralization, treatment with an alkali, distillation under reduced pressure, extraction with an organic solvent and crystallization from an organic solvent.

According to the present invention, by carrying out the oxidation of IPN in the presence of the peroxodisulfate in a mixed solvent of water and an organic polar solvent, as will be shown in Examples, HPN is available from IPN, and particularly by the use of the iron (II) salt and/or the chloride, it is possible to raise the conversion of IPN. As a result, HPN can be obtained in a higher yield as compared to the case where the iron (II) salt and the chloride are not used. Accordingly, it is possible according to the present invention to produce HPN industrially and profitably.

In this connection, as will be seen in Comparative Examples, in the case where IPN is subjected to oxidation by peroxodisulfate ions while using water alone as a medium, HPN is scarcely available.

The present invention will be explained more precisely while referring to the non-limitative Examples and Comparative Examples as follows.

EXAMPLE 1

Into a 500 ml-flask provided with a stirrer, 1.7 g (0.01 mol) of 2-isopropylnaphthalene, 100 ml of water and 100 ml of acetonitrile were introduced, and after heating the content of the flask to 77° C., 20 ml of an aqueous solution dissolving 4.6 g (0.02 mol) of ammonium peroxodisulfate was added to the flask over a period of 5 min under vigorous stirring of the content in an aerial atmosphere.

After heating the reaction mixture at 77° C. for 120 min under agitation, the reaction mixture was subjected to analysis by high performance liquid chromatography (HPLC). The results are shown in Table 1.

EXAMPLE 2

Into a 500 ml-flask provided with a stirrer, 5.3 g (0.025 mol) of 2,6-diisopropylnaphthalene, 60 ml of water and 120 ml of acetonitrile were introduced, and after heating the content of the flask to 75° C., 60 ml of an aqueous solution dissolving 17.1 g (0.075 mol) of ammonium peroxodisulfate was added to the flask from a dropping funnel over a period of 60 min while vigorously stirring the content of the flask under an aerial atmosphere. Thereafter, the reaction mixture was subjected to analysis by HPLC the results of analysis being shown in Table 2.

The HPNs produced in the reaction were as follows.
(1) 2-(2-hydroxy-2-propyl)-6-isopropylnaphthalene represented by the formula:

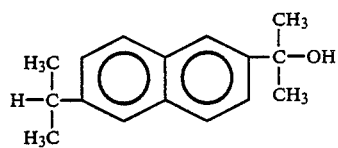

(2) 2,6-di(2-hydroxy-2-propyl)naphthalene represented by the formula:

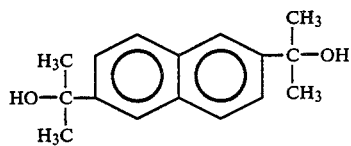

and (3) 2-(2-hydroxy-2-propyl)-6-acetylnaphthalene represented by the formula:

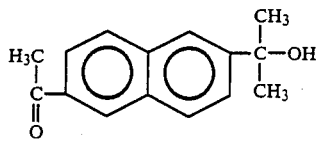

EXAMPLE 3

Into a 1-liter flask provided with a stirrer, 5.3 g (0.025 mol) of 2,6-diisopropylnaphthalene, 200 ml of water, 200 ml of acetonitrile and 34.2 g (0.15 mol) of ammonium peroxodisulfate were placed, and after heating the content of the flask to 65° C., it was kept at 65° C. for 25 min under vigorous stirring in an aerial atmosphere.

Thereafter, the reaction mixture was subjected to analysis by HPLC, the results being shown also in Table 2.

EXAMPLE 4

Into a 1-liter flask provided with a stirrer, 5.3 g (0.025 mol) of 2,6-diisopropylnaphthalene, 50 ml of water, 100 ml of acetonitrile and 5.8 g (0.1 mol) of sodium chloride were introduced, and after heating the content in the flask to 70° C., both 100 ml of an aqueous solution dissolving 34.2 g (0.15 mol) of ammonium peroxodisulfate and 200 ml of an aqueous solution dissolving 27.8 g (0.1 mol) of iron (II) sulfate heptahydrate was added to the flask from a dropping funnel over a period of 50 min under vigorous stirring in an aerial atmosphere. Thereafter, the reaction mixture was subjected to analysis by HPLC, the results being also shown in Table 2.

EXAMPLE 5

Into a 1-liter flask provided with a stirrer, 5.3 g (0.025 mol) of 2,6-diisopropylnaphthalene, 100 ml of water, 100 ml of acetonitrile, 34.2 g (0.15 mol) of ammonium peroxodisulfate and 5.8 g (0.1 mol) of sodium chloride were introduced, and after heating the content of the flask to 65° C., 50 ml of an aqueous solution dissolving 7.0 g (0.025 mol) of iron (II) sulfate heptahydrate was added to the flask from a dropping funnel over a period of 25 min under vigorous stirring in an aerial atmosphere.

Thereafter, the reaction mixture was subjected to analysis by HPLC, the results being also shown in Table 2.

EXAMPLE 6

Into a 1-liter flask provided with a stirrer, 10.6 g (0.05 mol) of 2,6-diisopropylnaphthalene, 200 ml of water, 200 ml of acetonitrile, 54.8 g (0.24 mol) of ammonium peroxodisulfate and 11.7 g (0.2 mol) of sodium chloride were introduced, and after heating the content of the flask to 65° C., 45 ml of an aqueous solution dissolving 6.3 g (0.023 mol) of iron (II) sulfate heptahydrate was added to the flask over a period of 45 min under vigorous stirring in an aerial atmosphere. Thereafter, the reaction mixture was subjected to analysis by HPLC, the results being also shown in Table 2.

EXAMPLE 7

In the same manner as in Example 6 except for using 57.1 g (0.24 mol) of sodium peroxodisulfate instead of 54.8 g (0.24 mol) of ammonium peroxodisulfate in Example 6, the same amount of 2,6-diisopropylnaphthalene as in Example 6 was subjected to reaction.

The results are also shown in Table 2.

EXAMPLE 8

Into a 1-liter flask provided with a stirrer, 10.6 g (0.05 mol) of 2,6-diisopropylnaphthalene, 200 ml of water, 200 ml of acetonitrile, 54.8 g (0.24 mol) of ammonium peroxodisulfate, and 23.4 g (0.4 mol) of sodium chloride were introduced, and after heating the content of the flask to 65° C., 55 ml of an aqueous solution dissolving 7.6 g (0.027 mol) of iron (II) sulfate heptahydrate was added to the flask from a dropping funnel over a period of 55 min under vigorous stirring in an aerial atmosphere. Thereafter, the reaction mixture was subjected to analysis by HPLC. The results are shown also in Table 2.

EXAMPLE 9

Into a 1-liter flask provided with a stirrer, 5.3 g (0.025 mol) of 2,6-diisopropylnaphthalene, 200 ml of water, 200 ml of acetonitrile, 34.2 g (0.15 mol) of ammonium peroxodisulfate and 5.8 g (0.1 mol) of sodium chloride were introduced, and after heating the content of the flask to 65° C., it was kept for 25 min at the temperature under vigorous stirring in an aerial atmosphere. Thereafter, the reaction mixture was analyzed by HPLC, the results being shown also in Table 2.

EXAMPLE 10

After introducing 5.3 g (0.025 mol) of 2,6-diisopropylnaphthalene, 200 ml of water, 200 ml of acetonitrile, 34.2 g (0.15 mol) of ammonium peroxodisulfate and 5.8 g (0.1 mol) of sodium chloride into a 1-liter flask provided with a stirrer and heating the thus placed substances to 65° C., 50 ml of an aqueous solution dissolving 7.0 g (0.025 mol) of iron (II) sulfate heptahydrate was added to the flask from a dropping funnel over a period of 25 min under vigorous stirring in an aerial atmosphere. Thereafter, the reaction mixture was subjected to analysis by HPLC, the results being also shown in Table 2.

Comparing the results of Example 10 with those of Example 9, it will be clearly seen that the presence of Fe(II) ions shows a remarkable effect in the improvement of the yield of the object product (HPN).

EXAMPLE 11

After introducing 5.3 g (0.025 mol) of 2,6-diisopropylnaphthalene, 200 ml of water, 200 ml of acetonitrile and 34.2 g (0.15 mol) of ammonium peroxodisulfate into a 2-liter flask provided with a stirrer, and heating the content of the flask to 55° C., 250 ml of an aqueous solution dissolving 34.8 g (0.125 mol) of iron (II) sulfate heptahydrate was added to the flask over a period of 125 min under vigorous stirring in an aerial atmosphere. Thereafter, the reaction mixture was subjected to analysis by HPLC the results being also shown in Table 2.

EXAMPLE 12

In the same manner as in Example 11 except for further introducing 5.8 g (0.1 mol) of sodium chloride into the flask, the same amount of 2,6-diisopropylnaphthalene as in Example 11 was subjected to reaction, the results being shown also in Table 2.

Comparing the results of Example 12 with those of Example 11, it will be clearly seen that the presence of chloride ions in the reaction system shows a remarkable effect in improving the yield of the object product (HPN).

The following Comparative Examples show the cases of the reaction of IPN without using the organic polar solvent.

COMPARATIVE EXAMPLE 1

After introducing 5.3 g (0.025 mol) of 2,6-diisopropylnaphthalene, 400 ml of water, 34.2 g (0.15 mol) of ammonium peroxodisulfate and 5.8 g (0.1 mol) of sodium chloride into a 1-liter flask provided with a stirrer and heating the content of the flask to 70° C., 200 ml of an aqueous solution dissolving 27.8 g (0.1 mol) of iron (II) sulfate heptahydrate was added to the flask from a dropping funnel over a period of 100 min under vigorous stirring in an aerial atmosphere.

Thereafter, the reaction mixture was subjected to analysis by HPLC to find that only 2-(2-hydroxy-2-propyl)-6-isopropylnaphthalene was produced in a poor yield as the reaction product, the results being also shown in Table 2.

COMPARATIVE EXAMPLE 2

After introducing 5.3 g (0.025 mol) of 2,6-diisopropylnaphthalene, 400 ml of water and 34.2 g (0.15 mol) of ammonium peroxodisulfate into a 1-liter flask provided with a stirrer, and heating the content of the flask to 70° C., it was kept at 70° C. for 100 min under vigorous stirring in an aerial atmosphere. As a result of analyzing the reaction mixture by HPLC, it was found that the reaction product was the same as that in Comparative Example 1, the results being shown also in Table 2.

Comparing the results of Comparative Examples 1 and 2 with those of Examples, it will be clearly seen that acetonitrile shows an extremely remarkable effect in improving the yield of the object product.

EXAMPLE 13

After introducing 1.1 g (0.005 mol) of 2,6-diisopropylnaphthalene, 50 ml of water, 50 ml of acetone, 6.8 g (0.03 mol) of ammonium peroxodisulfate and 1.2 g (0.02 mol) of sodium chloride into a 500-ml flask provided with a stirrer and heating the content of the flask to 57° C., 50 ml of an aqueous solution dissolving 2.8 g (0.01 mol) of iron (II) sulfate heptahydrate was added to the flask from a dropping funnel over a period of 50 min under vigorous stirring in an aerial atmosphere.

Thereafter, the reaction mixture was subjected to analysis by HPLC, the results being also shown in Table 2.

EXAMPLE 14

After introducing 1.1 g (0.005 mol) of 2,6-diisopropylnaphthalene, 50 ml of water, 50 ml of acetic acid, 6.8 g (0.03 mol) of ammonium peroxodisulfate and 1.2 g (0.02 mol) of sodium chloride into a 500-ml flask provided with a stirrer and heating the content of the flask to 65° C., 25 ml of an aqueous solution dissolving 1.4 g (0.005 mol) of iron (II) sulfate heptahydrate was added to the flask from a dropping funnel over a period of 25 min under vigorous stirring in an aerial atmosphere.

Thereafter, the reaction mixture was subjected to analysis by HPLC, the results being also shown in Table 2.

EXAMPLE 15

After introducing 1.1 g (0.005 mol) of 2-isopropylnaphthalene-6-carboxylic acid, 40 ml of water, 40 ml of acetonitrile, 3.4 g (0.015 mol) of ammonium peroxodisulfate and 5.8 g (0.1 mol) of sodium chloride into a 300 ml-flask provided with a stirrer and heating the content of the flask to 70° C., 30 ml of an aqueous solution dissolving 2.1 g (0.0076 mol) of iron (II) sulfate heptahydrate was added to the flask from a dropping funnel over a period of 60 min under vigorous stirring in an aerial atmosphere. Thereafter, the reaction mixture was subjected to analysis by HPLC, the results being also shown in Table 3.

TABLE 1

| Example | Reaction temperature (°C.) | Organic polar solvent | Use of $Fe^{2+}$ | Use of $Cl^-$ | Conversion of (2-isopropylnaphthalene) (%) | Selectivity* of (2-(2-hydroxy-2-propyl)naphthalene) (%) | Yield (%) |
|---|---|---|---|---|---|---|---|
| 1 | 77 | $CH_3CN$ | no | no | 80 | 82 | 66 |

Note:
Selectivity = $\dfrac{\text{the mols of the produced 2-(2-hydroxy-2-propyl)naphthalene}}{\text{the mols of the reacted 2-isopropylnaphthalene}} \times 100$

TABLE 2

| Example | Reaction temperature (°C.) | Organic polar solvent | Use of $Fe^{2+}$ | Use of $Cl^-$ | Conversion of 2,6-diisopropyl-naphthalene | A 2-(2-hydroxy-2-propyl)-6-isopropyl-naphthalene | B 2,6-di(2-hydroxy-2-propyl)-naphthalene | C 2-(2-hydroxy-2-propyl)-6-acetylnaphthalene | A + B + C | Yield of A + B + C (%) |
|---|---|---|---|---|---|---|---|---|---|---|
| 2 | 75 | $CH_3CN$ | no | no | 53 | 64 | 16 | 3 | 83 | 43 |
| 3 | 65 | $CH_3CN$ | no | no | 42 | 52 | 11 | 2 | 65 | 27 |
| 4 | 70 | $CH_3CN$ | yes | yes | 66 | 25 | 52 | 8 | 85 | 56 |
| 5 | 65 | $CH_3CN$ | yes | yes | 96 | 21 | 65 | 1 | 87 | 84 |
| 6 | 65 | $CH_3CN$ | yes | yes | 99 | 9 | 73 | 7 | 89 | 88 |
| 7 | 65 | $CH_3CN$ | yes | yes | 99 | 12 | 70 | 7 | 89 | 88 |
| 8 | 65 | $CH_3CN$ | yes | yes | 98 | 10 | 79 | 0 | 89 | 87 |
| 9 | 65 | $CH_3CN$ | no | yes | 52 | 57 | 16 | 0 | 73 | 38 |
| 10 | 65 | $CH_3CN$ | yes | yes | 100 | 2 | 74 | 6 | 82 | 82 |
| 11 | 55 | $CH_3CN$ | yes | no | 48 | 36 | 32 | 3 | 71 | 34 |
| 12 | 55 | $CH_3CN$ | yes | yes | 95 | 16 | 65 | 6 | 87 | 83 |

TABLE 2-continued

| Example | Reaction temperature (°C.) | Organic polar solvent | Use of Fe²⁺ | Use of Cl⁻ | Conversion of 2,6-diisopropyl-naphthalene | Selectivity* (%) A 2-(2-hydroxy-2-propyl)-6-isopropyl-naphthalene | B 2,6-di(2-hydroxy-2-propyl)-naphthalene | C 2-(2-hydroxy-2-propyl)-6-acetylnaphthalene | A + B + C | Yield of A + B + C (%) |
|---|---|---|---|---|---|---|---|---|---|---|
| 13 | 57 | CH₃COCH₃ | yes | yes | 71 | 28 | 57 | 0 | 85 | 63 |
| 14 | 65 | CH₃COOH | yes | yes | 54 | 12 | 37 | 0 | 49 | 26 |
| Comparative Example 1 | 70 | not used | yes | yes | 15 | 7 | 0 | 0 | 7 | 1 |
| Comparative Example 2 | 70 | not used | no | no | 14 | 13 | 0 | 0 | 13 | 2 |

Note:
Selectivity = (the mols of each of the produced HPNs / the mols of the reacted 2,6-diisopropylnaphthalene) × 100

TABLE 3

| Example | Reaction temperature (°C.) | Organic polar solvent | Use of Fe²⁺ | Use of Cl⁻ | Conversion of 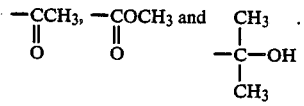 (%) | Selectivity* of 2-(2-hydroxy-2-propyl)naphthalene-6-carboxylic acid (%) | Yield (%) |
|---|---|---|---|---|---|---|---|
| 15 | 70 | CH₃CN | yes | yes | 81 | 65 | 53 |

Note:
Selectivity = (the mols of the produced 2-(2-hydroxy-2-propyl)naphthalene-6-carboxylic acid / the mols of the reacted 2-isopropylnaphthalene-6-carboxylic acid) × 100

What is claimed is:

1. A process for producing a (2-hydroxy-2-propyl)-naphthalene compound which comprises the step of oxidizing a naphthalene compound having at least one isopropyl group on the naphthalene ring in the presence of 0.05 to 10 mols of peroxodisulfate per mol of the isopropyl group in the reaction system at a temperature of 0° to 120° C. in a mixed solvent of water and an organic polar solvent, the naphthalene compound being naphthalene or a substituted naphthalene derivative having one or more substituents selected from the group consisting of —COOH, $$-CCH_3, \quad -COCH_3 \quad \text{and} \quad -\underset{\underset{CH_3}{|}}{\overset{\overset{CH_3}{|}}{C}}-OH$$
$$\underset{O}{\|} \quad \underset{O}{\|}$$

2. A process according to claim 1, wherein said oxidation is carried out in the presence of iron (II) salt and/or chloride.

3. A process according to claim 1, wherein said organic polar solvent is acetonitrile, acetone or acetic acid.

4. A process according to claim 1, wherein said peroxodisulfate is ammonium peroxodisulfate, sodium peroxodisulfate or potassium peroxodisulfate.

5. A process according to claim 2, wherein said iron (II) salt is iron (II) sulfate heptahydrate or iron (II) chloride.

6. A process according to claim 2, wherein said chloride is sodium chloride.

7. A process according to claim 2, wherein said iron (II) salt are used in an amount of not less than 0.001 mol per one mol of said isopropyl group.

8. A process according to claim 2, wherein said chloride are used in an amount of not less than 0.01 mol as chloride ion per one mol of said isopropyl group.

* * * * *